United States Patent [19]

Herrmann et al.

[11] Patent Number: 5,882,674
[45] Date of Patent: Mar. 16, 1999

[54] TRANSDERMAL THERAPEUTIC SYSTEM COMPRISING ACTIVE SUBSTANCES REPRESENTING CARBON MONOXIDE SOURCES

[75] Inventors: Fritz Herrmann; Harald List, both of Neuwied, Germany

[73] Assignee: LTS Lohmann Therapie-Systeme GmbH, Neuwied, Germany

[21] Appl. No.: 765,581

[22] PCT Filed: Jun. 3, 1995

[86] PCT No.: PCT/EP95/02119

§ 371 Date: Dec. 16, 1996

§ 102(e) Date: Dec. 16, 1996

[87] PCT Pub. No.: WO95/35105

PCT Pub. Date: Dec. 28, 1995

[30] Foreign Application Priority Data

Jun. 18, 1994 [DE] Germany .......................... 44 21 433.2

[51] Int. Cl.⁶ ...................................... A61F 13/02
[52] U.S. Cl. .......................... 424/448; 424/449; 514/822; 514/885
[58] Field of Search ..................... 424/448, 449; 514/822, 885

[56] References Cited

U.S. PATENT DOCUMENTS

| | | | |
|---|---|---|---|
| 3,598,122 | 8/1971 | Zaffaroni | 128/268 |
| 4,687,481 | 8/1987 | Nuwayser | 604/897 |
| 4,708,716 | 11/1987 | Sibalis | 604/20 |
| 5,308,625 | 5/1994 | Wong | 424/449 |

FOREIGN PATENT DOCUMENTS

| | | | |
|---|---|---|---|
| 3 315 272 | 10/1984 | Germany . | |
| 91/01128 | 2/1991 | WIPO | A61K 7/48 |
| 91/01301 | 2/1991 | WIPO | A61K 31/215 |

OTHER PUBLICATIONS

Heilmann, *Therapeutische Systeme,* Ferdinand Enk, Verlag Stuttgart, Germany 1982 p. 26.

*Primary Examiner*—D. Gabrielle Brouillette
*Attorney, Agent, or Firm*—Wenderoth, Lind & Ponack, L.L.P.

[57] ABSTRACT

A transdermal therapeutic system (TTS) comprises compounds releasing carbon monoxide in organisms to increase the CO-concentration in the organism.

13 Claims, No Drawings

TRANSDERMAL THERAPEUTIC SYSTEM COMPRISING ACTIVE SUBSTANCES REPRESENTING CARBON MONOXIDE SOURCES

This application is a 371 of PCT/EP95/02119, filed Jun. 03, 1995.

BACKGROUND OF THE INVENTION

The present invention relates to a transdermal therapeutic system (TTS) for the systemic and topical administration of active substances which are suitable to increase the carbon monoxide (CO) concentration in the organism.

Many research works carried out quite recently have shown that CO is of very great importance as a mediator in both physiological and physiopathological processes in the body. This part of CO comprises the regulation of the arterial tone of the vessels, the blood platelet aggregation, the influence on immunological and inflammatory processes, and the function as a messenger substance in the transmission of impulses of the central and peripheral nervous system. CO is also included in physiopathological changes of these functional structures or organ systems; for example, hypertension, coronary stenoses, arteriosclerosis. Moreover, there are indications as to a participation in immunological and inflammatory reactions and to an influence on cell growth.

In addition to the vasodilative and antithrombotic action, CO is said to have the function of a neurotransmitter in the central and peripheral nervous system. The important role as an intercellular and intracellular mediator is rendered possible by the rapid diffusion through cell membranes.

Owing to this finding there is the demand of being able to supply the active substance CO to the organism in a controllable manner without provoking the risk of an intoxication by accumulation to the hemoglobin. The way via the respiratory air, which normally comprises more or less CO, is ruled out because an exact and, in particular, reproducible dosage is difficult to manage. Other parenteral or eternal methods of administration are not known.

BRIEF SUMMARY OF THE INVENTION

It is accordingly the object of the present invention to provide a transdermal therapeutic administration system for active substances which supply human or animal organisms with CO in a specific and reproducible active substance dosage.

This object is achieved by the fact that active substances are administered to an organism through the skin or mucosa by means of a transdermal therapeutic system, and that at least one of the active substances is selected from compounds releasing carbon monoxide (CO) in organisms.

DETAILED DESCRIPTION OF THE INVENTION

A therapeutic system is a drug-containing device or form of administration which continuously releases one or several drugs at a predetermined rate over a definite period of time to a definite site of application (HEILMANN "Therapeutische Systeme", F. Enke Verlag Stuttgart, 1982, p. 26). Therapeutic systems can be used for both topical and systemic applications, and accordingly they have different conceptions.

Among other things, a transdermal therapeutic system according to the present invention is characterized by the following advantages:

The supply of CO to the organism via the respiratory air is avoided.

The active substance directly reaches the systemic circulation in its pharmacologically active form, avoiding metabolism in the gastrointestinal tract.

Reduction of gastrointestinal side effects.

Uniform therapeutic action with minimized dose, as compared to other administration routes.

Particular suitability for active substances having a very short pharmacodynamic phase.

Ambulatory treatment of the patients without necessity of permanent control.

Improved patient compliance.

There are many possibilities of realizing a TTS comprising the active substance(s) according to the present invention; for example, pressure-sensitive adhesive patches, films, sprays, creams, ointments, and the like. The administration form of a pressure-sensitive adhesive patch is particularly preferable. In general, it consists of an impermeable backing layer; an active substance reservoir connected therewith and having a mostly polymeric matrix; in the absence of other control mechanisms, a membrane controlling the active substance release; a pressure-sensitive adhesive device to fix the system on the skin; and, if required, a protective layer removable prior to applying the system as a ready-made drug.

The transdermal pressure-sensitive adhesive patches which can be used for the present invention are known to the skilled artisan from the prior art. Essentially they can be classified into two basic control principles: matrix-diffusion-control and membrane control, only the last-mentioned having a zero-order active substance release. A patch having a matrix-diffusion-control is described in DE-PS 33 15 272, for example. This system consists of an impermeable backing layer; a specially constructed reservoir connected therewith, made of a polymer matrix, and comprising the active substance in a concentration above the saturation concentration; an adhesive layer connected with the reservoir and permeable to the active substance; and a protective layer which covers the pressure-sensitive adhesive layer and is removed for use. If the reservoir matrix itself is pressure-sensitive adhesive, the additional pressure-sensitive adhesive layer is not necessary.

U.S. Pat. No. 3,598,122 is an example describing patches having a membrane control. These patches basically consist of a backing layer representing one of the surfaces, an adhesive layer which is permeable to the active substance and represents the other surface, and finally a reservoir comprising the active substance between the two layers forming the surfaces. Alternatively, the active substance may be contained in a great number of microcapsules which are distributed within the permeable adhesive layer. Here, the active substance is continuously released from the reservoir or the microcapsules through a membrane into the adhesive layer which is permeable to the active substance and in contact with the patient's skin. If microcapsules are used, the capsule material may also act as a membrane.

Additionally, it is also possible to use electric current for controlling purposes; in this case, the rate is determined by the penetration of the active substance through the skin. Such processes are referred to as electroosmosis, iontophoresis, or electrophoresis. In addition to the matrix forming the reservoir and the active substance or active substance combinations, the patches—irrespective of their nature—may comprise various additives, if required. Additives influencing the active substance diffusion in the reservoir and/or the active substance permeation through the skin are particularly worth mentioning. These additives are known to experts in this field.

Above all, CO-containing complex compounds falling under the generic term coordination compounds are to be mentioned as suitable active substances for the present invention. Here, CO presents itself as a ligand linked with a central atom. Addition complexes are given preference over penetration complexes because of easier cleavability. In general, these addition complexes are solid or liquid substances whose weight is easy to handle and which can therefore be incorporated into a TTS in a defined concentration. These coordination compounds have at least one CO-ligand; but there are also polynuclear representatives which have up to 12 CO bound to them, for example. In addition to CO, other ligands may also be bound to the central atom. The term polynuclear coordination compounds is used to mean those having more than one central atom. These are also suitable according to the present invention. Coordination compounds having metals of the sixth to eighth subgroup of the periodic system as the central atom are particularly preferable; iron pentacarbonyl and iron enneacarbonyl being the most preferred. In addition to complex compounds exclusively containing CO as ligand, those compounds are also suitable which, in addition to CO, have further ligands known from coordination chemistry.

To produce the TTSs according to the present invention, an effective amount of active substance is incorporated into the system in solid or liquid form, in solution or in dispersion, and usual additives may be used. The selection of components, the construction, the design, and the active substance concentrations depend on the nature of the active substance and the desired effect. For this reason, it is not possible to give detailed information of universal validity.

The exclusive use of the TTSs according to the present invention is the production of ready-to-use drugs, preferably in the form of patches, to remedy a carbon monoxide deficiency in human or animal organisms. Consequences of this deficiency phenomenon include:

hypertension and/or angiospasms in arteries blood platelet aggregation disturbance of immunological reactions inflammatory processes disturbance of impulse transmission in the central and peripheral nervous system.

The following parameters, which are adapted to the intended purpose by the skilled artisan, must be determined from case to case when ready-to-use drugs in the form of patches are produced:

choice of the active substance active substance combination release control release rate composition of the reservoir stabilization addition of enhancers thickness of layers design of the backing layer dimensioning.

We claim:

1. A method for treating carbon monoxide deficiency in a human or animal organism in need of such treatment which comprises applying topically to said organism a transdermal therapeutic system containing at least one active substance which is capable of releasing carbon monoxide to the organism.

2. The method according to claim 1, wherein the active substance contains a coordination compound comprising carbon monoxide as at least one of the ligands.

3. The method according to claim 2, wherein the coordination compound additionally comprises ligands other than carbon monoxide.

4. The method according to claim 2, wherein the active substance contains a polynuclear coordination compound comprising carbon monoxide as at least one of the ligands.

5. The method according to claim 1, wherein the active substance contains a metal carbonyl coordination compound of a metal of the sixth to eighth subgroup of the periodic table, and has at least one CO group as a ligand.

6. The method according to claim 1, wherein at least one active substance is iron pentacarbonyl.

7. The method according to claim 1, wherein at least one active substance is iron enneacarbonyl.

8. The method according to claim 1, wherein the active substance is contained in an ointment, a cream, a gel, a colloid, or a pharmaceutical formulation comprising liposomes or niosomes.

9. The method according to claim 1, wherein the transdermal therapeutic system is in the form of a patch comprising an impermeable backing layer, an active substance reservoir connected therewith, a pressure-sensitive adhesive device to fix the system on the skin, a means for controlling the release of the active substance, and, optionally, a protective layer which is removable prior to application.

10. The method according to claim 9, wherein the means for controlling the release of the active substance comprises using electric current to enhance permeation of the active substance or active substances through the skin.

11. The method according to claim 9, wherein the means for controlling the release of the active substance comprises a membrane.

12. The method according to claim 1, wherein the transdermal therapeutic system further comprises at least one substance which improves the permeation of the active substance through the skin.

13. The method according to claim 1, wherein the active substance is microencapsulated.

* * * * *